United States Patent
Sih et al.

(10) Patent No.: US 7,702,388 B2
(45) Date of Patent: Apr. 20, 2010

(54) CARDIAC THERAPY TRIGGERED BY CAPTURE VERIFICATION

(75) Inventors: Haris J. Sih, Minneapolis, MN (US);
Scott A. Meyer, Rochester, MN (US);
Paul A. Haefner, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1625 days.

(21) Appl. No.: 10/377,257

(22) Filed: Feb. 28, 2003

(65) Prior Publication Data

US 2004/0172065 A1 Sep. 2, 2004

(51) Int. Cl.
*A61N 1/08* (2006.01)
*A61N 1/39* (2006.01)
(52) U.S. Cl. .................... 607/5; 607/4; 607/9
(58) Field of Classification Search ............ 607/4, 607/5, 9
See application file for complete search history.

(56) References Cited

U.S. PATENT DOCUMENTS

| | | | | |
|---|---|---|---|---|
| 5,282,836 A | | 2/1994 | Kreyenhagen et al. | 607/4 |
| 5,562,708 A | | 10/1996 | Combs et al. | 607/4 |
| 5,674,251 A | | 10/1997 | Combs et al. | 607/4 |
| 5,683,426 A | * | 11/1997 | Greenhut et al. | 607/9 |
| 5,776,164 A | * | 7/1998 | Ripart | 607/5 |
| 5,797,967 A | | 8/1998 | KenKnight | 607/4 |
| 6,081,746 A | | 6/2000 | Pendekanti et al. | 607/5 |
| 6,085,116 A | | 7/2000 | Pendekanti et al. | 607/5 |
| 6,154,672 A | | 11/2000 | Pendekanti et al. | 607/5 |
| 6,256,535 B1 | * | 7/2001 | Province et al. | 607/5 |
| 6,292,691 B1 | | 9/2001 | Pendekanti et al. | |
| 6,512,953 B2 | | 1/2003 | Florio et al. | |
| 6,754,525 B1 | * | 6/2004 | Province et al. | 607/4 |
| 2001/0049543 A1 | * | 12/2001 | Kroll | 607/28 |
| 2003/0163165 A1 | * | 8/2003 | Bornzin et al. | 607/5 |

OTHER PUBLICATIONS

"Capture of Atrial Fibrillation Reduces the Atrial Defibrillation Threshold." *Journal of Pacing and Clinical Electrophysiology*, Aug. 2002, vol. 25, No. 8., pp. 1159-1165.
Office Action from U.S. Appl. No. 11/300,674 dated Oct. 9, 2007, 9 pages.
Office Action from U.S. Appl. No. 11/300,674 dated May 30, 2008, 8 pages.
Office Action Response for U.S. Appl. No. 11/300,374, filed with U.S. Patent and Trademark Office on Mar. 13, 2009, pp. 1-7.

* cited by examiner

*Primary Examiner*—Carl H. Layno
*Assistant Examiner*—Tammie K. Heller
(74) *Attorney, Agent, or Firm*—Hollingsworth & Funk, LLC (57) ABSTRACT

The present disclosure provides methods and systems for tachyarrhythmia therapy involving pacing the heart to prior to the application of a cardioversion/defibrillation shock. One or more pace pulses are delivered to the arrhythmic chamber or chambers. The pace pulses may be delivered to the heart at an adaptable rate selected to organize the electrical activity of the heart. If the pace pulses produce capture, cardioversion/defibrillation stimulation is delivered.

43 Claims, 6 Drawing Sheets

CARDIAC THERAPY TRIGGERED BY CAPTURE VERIFICATION

FIELD OF THE INVENTION

The present invention relates generally to providing cardiac-therapy and, more particularly, to providing tachyarrhythmia therapy.

BACKGROUND OF THE INVENTION

When functioning normally, the heart produces rhythmic contractions and is capable of pumping blood throughout the body. However, due to disease or injury, the heart rhythm may become irregular resulting in diminished blood circulation. Arrhythmia is a general term used to describe heart rhythm irregularities arising from a variety of physical conditions and disease processes.

An abnormally fast heart rate is designated tachyarrhythmia. Tachyarrhythmias may originate in either the atria or the ventricles. Tachycardia is a term generally used to describe cardiac rhythms that are rapid, but relatively organized. Conversely, fibrillation is characterized by rapid, chaotic, and disorganized heart rhythms. Tachycardia and fibrillation may affect either the atria or the ventricles.

Pacemakers have been used as an effective treatment for patients with serious arrhythmias such as bradycardia, a condition characterized by an abnormally slow heart rate. Pacemakers typically include circuitry to sense electrical signals from the heart and a pulse generator for delivering a series of low energy electrical stimulation pulses to the heart. Leads extending into the patient's heart are connected to electrodes that contact the myocardium for sensing the heart's electrical signals and for delivering stimulation pulses to the heart. The pace pulses may be intermittent or continuous, depending on the patient's metabolic demand. The pace pulses are timed to assist the heart in producing a contractile rhythm that maintains cardiac pumping efficiency.

When a pace pulse produces a contractile response in heart tissue, the contractile response is typically referred to as capture, and the electrical cardiac signal corresponding to capture is denoted the evoked response. A pace pulse must exceed a minimum energy value, or capture threshold, to produce a contraction. Detection of the evoked response may be used to verify that the pace pulse has produced capture of the heart tissue.

Cardiac rhythm management systems may include both a pacemaker and a cardioverter/defibrillator. An implantable cardiac cardioverter/defibrillator (ICD) typically monitors cardiac activity and delivers high energy electrical stimulation to the heart to interrupt a tachycardia or fibrillation condition. In general, the ICD continuously monitors cardiac activity by analyzing electrical signals, known as electrograms (EGMs), detected by endocardial sensing electrodes. ICDs are generally capable of diagnosing the various types of tachyarrhythmias discussed above, and then delivering an appropriate electrical stimulation therapy to the patient's heart to terminate the diagnosed arrhythmia.

In general, atrial tachyarrhythmias are chronic conditions that are non-life threatening, because the atria only aid in the movement of blood into the ventricles, where the major pumping action of the heart occurs. Conversely, ventricular tachyarrhythmia is a life-threatening event because the heart's ability to pump blood to the rest of the body is seriously impaired if the ventricles become arrhythmic.

In the treatment of chronic cardiac conditions, such as atrial tachycardia or fibrillation, the patient is typically conscious and can feel the electrical stimulation applied to the heart. Thus, it is desirable to reduce the energy of the electrical stimulation for treating arrhythmias, particularly chronic atrial arrhythmias. For both atrial and ventricular tachyarrhythmias, the relative organizational state of the tachyarrhythmia may be related to the amount of energy needed for successful defibrillation therapy.

SUMMARY OF THE INVENTION

The present invention is directed to method and systems providing anti-tachyarrhythmia therapy. One embodiment of the invention involves a method for providing cardiac therapy to the heart. Pace pulses are delivered to an atrium during a tachyarrhythmic episode. Capture of the atrium associated with at least one of the pace pulses is detected. Cardioversion/defibrillation stimulation is delivered to the atrium responsive to the detection of capture.

In accordance with another embodiment of the invention, a method for providing therapy to a heart involves delivering pace pulses to the heart during a tachyarrhythmia episode. Capture of heart tissue associated with at least one of the pace pulses is detected. Cardioversion/defibrillation stimulation is delivered to the heart in response to detection of capture.

Yet another embodiment of the invention involves a system for treating cardiac arrhythmia. The system includes a lead system comprising electrodes and extending into the heart. Pulse generator circuitry is coupled to the lead system and configured to generate stimulation pulses to electrically stimulate the heart. A detector system coupled to the lead system is configured to sense cardiac signals transmitted through the lead electrodes. A control system, coupled to the detector system and the pulse generator, is configured to control the generation of pace pulses, to detect capture associated with at least one of the pace pulses, and to control the delivery of a cardioversion/defibrillation stimulation to the heart responsive to the detection of capture.

In accordance with another embodiment of the invention, a therapy system includes means for delivering pace pulses to an atrium of the heart during a tachyarrhythmia episode, means for detecting capture of the atrium associated with at least one of the pace pulses, and means for delivering cardioversion/defibrillation stimulation to the atrium responsive to the detection of capture.

In accordance with yet another embodiment of the invention, a system for providing therapy to a heart includes means for delivering pace pulses to the heart during a tachyarrhythmic episode, means for detecting capture associated with at least one of the pace pulses, and means for delivering a cardioversion/defibrillation stimulation in response to the verification of capture.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Pacing an arrhythmic heart chamber prior to the delivery of cardioversion/defibrillation shock can decrease the energy required for cardioversion or defibrillation. In accordance with principles of the invention, pacing can be used to organize the electrical cardiac activity so that lower cardioversion/defibrillation energy may be used to terminate the tachyarrhythmia. The present invention describes various methods and systems for triggering cardioversion/defibrillation therapy using capture verification following the application of one or more pace pulses to the arrhythmic chamber or chambers. In accordance with various embodiments, pace pulses are delivered to a heart chamber during a tachyarrhythmia episode. Upon verification of capture of the heart chamber, cardioversion/defibrillation stimulation is applied to terminate the arrhythmia.

The pace pulses may be delivered to the heart chamber in a timed relationship with the tachyarrhythmic activity. For example, the pacing pulses may be delivered at an adaptable frequency selected to produce capture in the arrhythmic heart chamber and/or to organize the electrical activity of the heart chamber. Prior to delivering cardioversion/defibrillation stimulation, the system determines if the pace pulses produce capture in the tachyarrhythmic chamber.

A cardiac cycle length may be measured and used to determine an effective pacing rate to effect capture and organize the arrhythmic condition. In one embodiment, a pacing interval is selected as a percentage of the cardiac cycle length. The pacing rate may be further modified based on current capture status. If the pace pulses delivered at the selected pacing interval do not consistently capture the arrhythmic heart chamber, the pacing interval may be modified to promote capture. When capture occurs consistently, the heart chamber is said to be entrained by the pace pulses. If the pace pulses entrain the electrical activity of the heart chamber, the pacing interval may be adapted to improve organization of the tachyarrhythmic activity. For example, if entrainment is detected, the pacing interval may be lengthened to slow the tachyarrhythmic activity.

The embodiments of the present invention illustrated herein are generally described as being implemented in an implantable cardiac defibrillator (ICD) that may operate in numerous pacing modes known in the art. Various types of single and multiple chamber implantable cardiac defibrillators are known in the art and may implement a capture verification methodology of the present invention. The systems and methods of the present invention may also be implemented in a variety of implantable or external therapeutic cardiac rhythm management systems, including single and multi chamber pacemakers, resynchronizers, and cardioverter/defibrillator systems, for example. Furthermore, the systems and methods of the invention may be implemented in diagnostic cardiac devices, such as cardiac monitors and the like, in combination with devices that stimulate the heart.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

Figure 1:
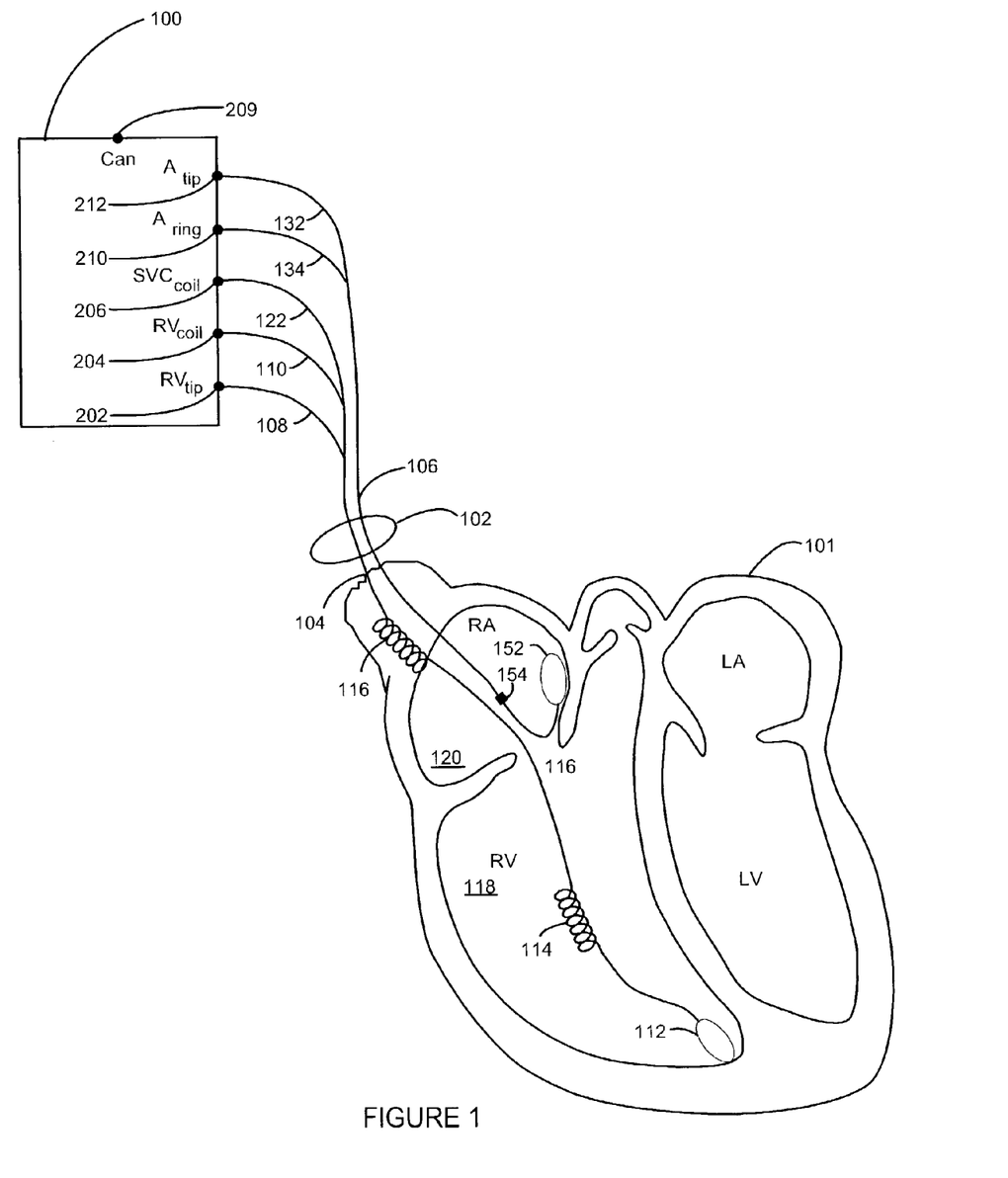
FIG. 1 is a partial view of one embodiment of an implantable medical device with an endocardial lead system extending into atrial and ventricular chambers of a heart.

Referring now to FIG. 1 of the drawings, there is shown one embodiment of a cardiac rhythm management system that includes an implantable cardiac defibrillator 100 electrically and physically coupled to an intracardiac lead system 102. The intracardiac lead system 102 is implanted in a human body with portions of the intracardiac lead system 102 inserted into a heart 101. The intracardiac lead system 102 is used to detect and analyze electrical cardiac signals produced by the heart 101 and to provide electrical energy to the heart 101 under certain predetermined conditions to treat cardiac arrhythmias, including, for example, ventricular fibrillation of the heart 101.

The intracardiac lead system 102 includes one or more pacing electrodes and one or more defibrillation electrodes. In the particular embodiment shown in FIG. 1, the intracardiac lead system 102 includes a ventricular lead system 104 and an atrial lead system 106. The ventricular lead system 104 may include an SVC-coil 116, an RV-coil 114, and an RV-tip electrode 112. The RV-coil 114, which may alternatively be an RV-ring electrode, is spaced apart from the RV-tip electrode 112, which is a pacing electrode. In one embodiment, the ventricular lead system 104 is configured as an integrated bipolar pace/shock lead. In another exemplary configuration, one or more additional electrodes, e.g., a ring electrode, may be included in the ventricular lead system 104. The additional ring electrode and the RV-tip electrode 112 may be used for bipolar sensing of cardiac signals. The atrial lead system 106 includes an A-tip electrode 152 and an A-ring electrode 154. In one embodiment, the atrial lead system 106 is configured as an atrial J lead.

In this configuration, the intracardiac lead system 102 is positioned within the heart 101, with portions of the atrial lead system 106 extending into the right atrium 120 and portions of the ventricular lead system 104 extending into the right atrium 120 and right ventricle 118. In particular, the A-tip electrode 152 and A-ring electrode 154 are positioned at appropriate locations within the right atrium 120. The RV-tip electrode 112 and RV-coil 114 electrodes are positioned at appropriate locations within the right ventricle 118. The SVC-coil 116 is positioned at an appropriate location within the right atrium chamber 120 of the heart 101 or a major vein leading to the right atrium chamber 120 of the heart 101. The RV-coil 114 and SVC-coil 116 depicted in FIG. 1 are defibrillation electrodes.

Additional pacing and defibrillation electrodes may also be included in the intracardiac lead system 102 to allow for various bipolar sensing, pacing, and defibrillation capabilities. For example, the intracardiac lead system 102 may include endocardial sensing, pacing, and/or cardioversion/defibrillation leads (not shown) that are advanced into the coronary sinus and coronary veins to locate the distal electrode(s) adjacent to the left ventricle or the left atrium. Other intracardiac lead and electrode arrangements and configurations known in the art are also possible and considered to be within the scope of the present system.

The ventricular and atrial lead systems 104, 106 include conductors for communicating sense signals and stimulation pulses between the cardiac defibrillator 100 and the electrodes and coils of the lead systems 104, 106. As is shown in FIG. 1, ventricular lead system 104 includes a conductor 108 for transmitting sense signals and stimulation pulses between the RV-tip electrode 112 and an RV-tip terminal 202 of the cardiac defibrillator 100. A conductor 110 of the ventricular lead system 104 transmits sense signals and/or stimulation pulses between the RV-coil electrode 114 and an RV-coil terminal 204 of the cardiac defibrillator 100. The ventricular lead system 104 also includes a conductor 122 for transmitting sense signals and/or stimulation pulses between and SVC coil terminal 206 of the cardiac defibrillator 100 and the SVC coil 116. The atrial lead system 106 includes conductors 132, 134 for transmitting sense and stimulation signals between terminals 212, 210 of the cardiac defibrillator 100 and A-tip and A-ring electrodes 152 and 154, respectively.

Figure 2:
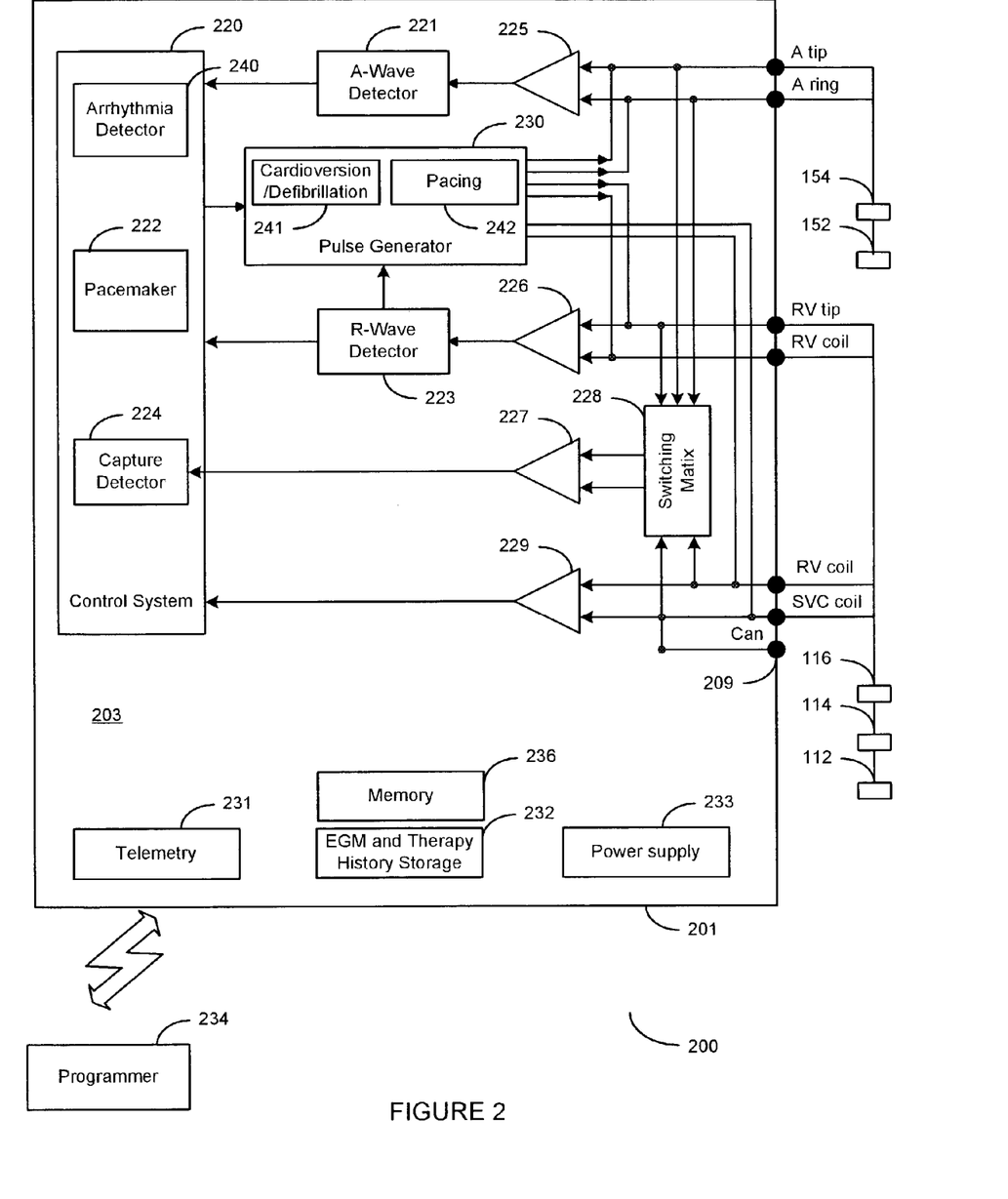
FIG. 2 is a block diagram of an implantable medical device with which anti-tachyarrhythmia therapy methods may be implemented in accordance with embodiments of the present invention.

Referring now to FIG. 2, there is shown an embodiment of a cardiac defibrillator 200 suitable for implementing a capture verification methodology of the present invention. FIG. 2 shows a cardiac defibrillator divided into functional blocks. It is understood by those skilled in the art that there exist many possible configurations in which these functional blocks can be arranged. The example depicted in FIG. 2 is one possible functional arrangement. The cardiac defibrillator 200 includes circuitry for receiving cardiac signals from a heart (not shown in FIG. 2) and delivering electrical stimulation energy to the heart.

In one embodiment, the cardiac defibrillator circuitry 203 of the cardiac defibrillator 200 is encased and hermetically sealed in a housing 201 suitable for implanting in a human body as is known in the art. Power to the cardiac defibrillator 200 is supplied by an electrochemical battery 233 that is housed within the cardiac defibrillator 200. The cardiac defibrillator 200 includes a connector block attached to the housing 201 of the cardiac defibrillator 200. Terminals of the connector block allow for the physical and electrical attachment of the intracardiac lead system conductors to the cardiac defibrillator 200 and the encased cardiac defibrillator circuitry 203, as previously discussed.

The cardiac defibrillator circuitry 203 of the cardiac defibrillator 200 may be a programmable microprocessor-based system, including a control system 220 and a memory circuit 236. The memory circuit 236 stores parameters for various pacing, defibrillation, and sensing modes, and stores data indicative of cardiac signals received by other components of the cardiac defibrillator circuitry 203. The control system 220 and memory circuit 236 cooperate with other components of the cardiac defibrillator circuitry 203 to perform operations involving therapy delivery based on capture verification according to the principles of the present invention, in addition to other sensing, pacing and defibrillation functions. The control system 220 may encompass additional elements, including a pacemaker 222, and an arrhythmia detector 240, along with other functional components, for controlling the cardiac defibrillator circuitry 203. A memory 232 is also provided for storing historical EGM and therapy data. The historical data may be used for various purposes to control the operations of the cardiac defibrillator 200 and may also be transmitted to an external programmer unit 234 as needed or desired.

Telemetry circuitry 231 is additionally coupled to the cardiac defibrillator circuitry 203 to allow the cardiac defibrillator 200 to communicate with an external programmer unit 234. In one embodiment, the telemetry circuitry 231 and the programmer unit 234 use a wire loop antenna and a radio frequency telemetric link, as is known in the art, to receive and transmit signals and data between the programmer unit 234 telemetry circuitry 231. In this manner, programming commands may be transferred to the control system 220 of the cardiac defibrillator 200 from the programmer unit 234 during and after implant. In addition, stored cardiac data pertaining to the functioning of the heart, along with other data, may be transferred to the programmer unit 234 from the cardiac defibrillator 200, for example.

Cardiac signals sensed through use of the RV-tip electrode 112 may be sensed as near-field signals as are known in the art. More particularly, a near-field signal may be detected as a voltage developed between the RV-tip electrode 112 and the RV-coil 114. Cardiac signals sensed through use of one or both of the defibrillation coils or electrodes 114, 116 are far-field cardiac signals, as are known in the art. More particularly, for example, a far-field signal is detected as a voltage developed between the RV-coil 114 and the SVC-coil 116.

A far-field cardiac signal may be detected as a voltage developed between the RV-coil 114 and the can electrode 209. Alternatively, the can electrode 209 and the SVC-coil electrode 116 may be shorted and the cardiac signal sensed as the voltage developed between the RV-coil 114 and the can electrode 209/SVC-coil 116 combination. Cardiac signals developed using appropriate combinations of the RV-coil, SVC-coil, and can electrodes 114, 116 and 209 are sensed and amplified by an EGM amplifier 229. The output of the EGM amplifier 229 is coupled to the control system 220.

In the embodiment of the cardiac defibrillator 200 depicted in FIG. 2, RV-tip and RV-coil electrodes 112, 114 are shown coupled to a V-sense amplifier 226 and thus to an R-wave detector 223. Cardiac signals received by the V-sense amplifier 226 are communicated to the R-wave detector 223, which serves to sense and amplify the cardiac signals, e.g. R-waves. The sensed R-waves may then be communicated to the control system 220.

A-tip and A-ring electrodes 152, 154 are shown coupled to an A-sense amplifier 225. Atrial sense signals received by the A-sense amplifier 225 are communicated to an A-wave detector 221, which serves to sense and amplify the A-wave signals. The atrial signals may be communicated from the A-wave detector 221 to the control system 220.

The pacemaker 222 communicates pacing signals to the RV-tip and A-tip electrodes 112 and 152 according to a pre-established pacing regimen under appropriate conditions. Blanking circuitry (not shown) is employed in a known manner when a ventricular or atrial pacing pulse is delivered, such that the ventricular or atrial channels are properly blanked at the appropriate time and for the appropriate duration.

A switching matrix 228, according to one embodiment, may be coupled to the A ring 154, RV tip 112, RV coil 114 and SVC coil 116 electrodes. The switching matrix 228 can be arranged to provide connections to various configurations of pacing and defibrillation electrodes. The outputs of the switching matrix 228 are coupled to an evoked response (ER) amplifier 227 which serves to sense and amplify signals detected between the selected combinations of electrodes. The detected signals are coupled through the ER amplifier to a capture detector 224. The capture detector 224 includes circuitry configured to detect an evoked response produced by a pace pulse.

The cardiac defibrillator 200 depicted in FIG. 2 is well-suited for implementing a tachyarrhythmia therapy methodology according to the principles of the present invention. In the embodiment illustrated in FIG. 2, the arrhythmia detector 240 receives signals representing cardiac activity and detects arrhythmias of the heart. The capture detection processes of the present invention are primarily carried out by the capture detector 224 in cooperation with other components of the control system 220.

Among other functions, the control system 220 controls the delivery of therapy to terminate a tachyarrhythmia of the heart in accordance with the principles of the invention. The therapy may include, for example, delivering low energy pace pulses to the heart using the pacemaker control circuitry 222 and the pace pulse generator 242 located in the pulse generator 230. Furthermore, the therapy may include delivering high energy cardioversion/defibrillation pulses to one or more heart chambers using the cardioverter/defibrillator pulse generator 241 triggered by detection of capture.

Figure 3:
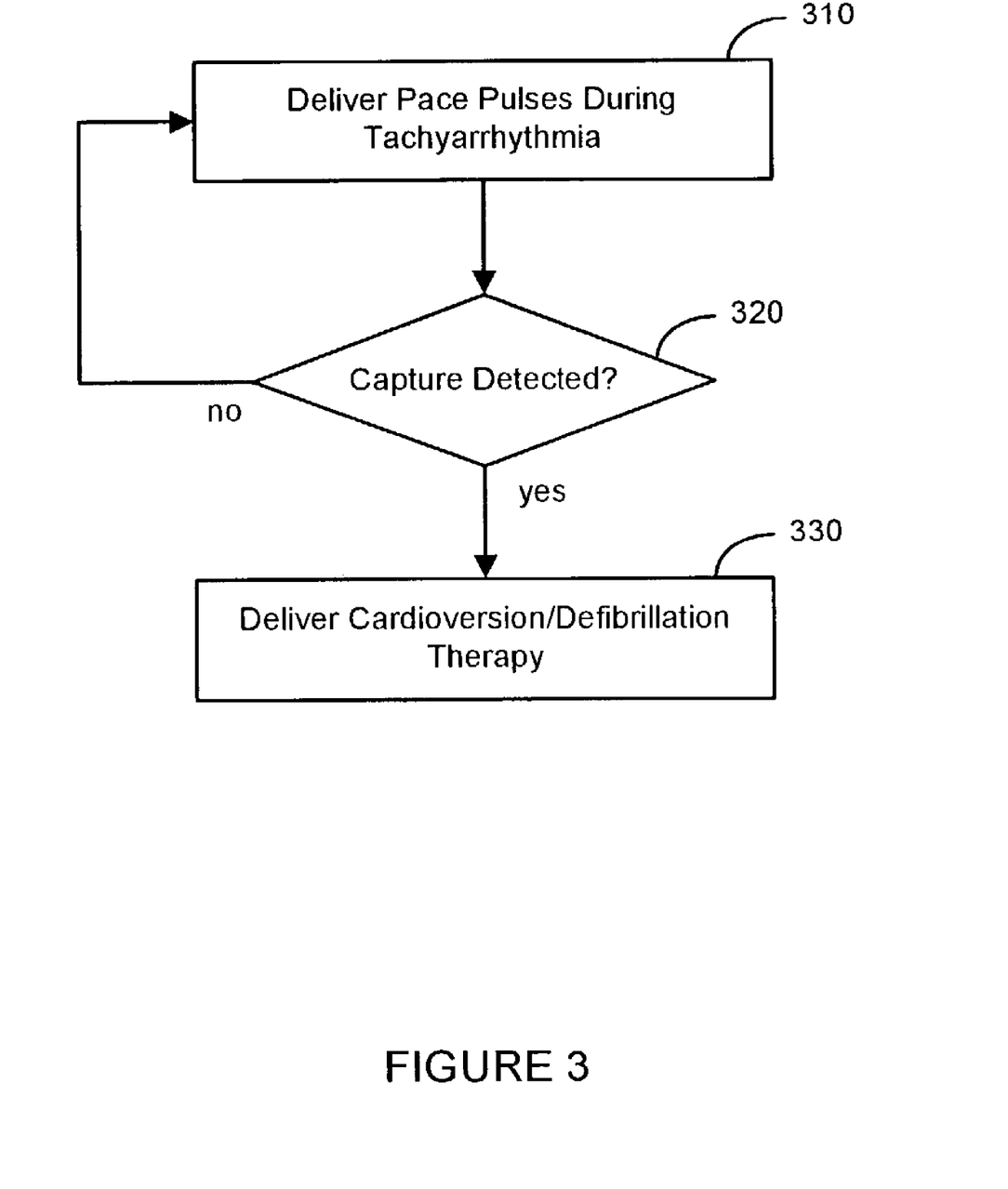
FIG. 3 is a flowchart of a method of providing cardiac therapy in accordance with embodiments of the present invention.

FIG. 3 is a flowchart illustrating a method of providing tachyarrhythmia therapy in accordance with embodiments of the invention. Following identification of a tachyarrhythmic episode, one or more pace pulses are delivered 310 to the arrhythmic chamber during the tachyarrhythmic episode. The energy of the pace pulses may be selected to produce capture of the arrhythmic tissue. The pace pulses are delivered at an energy above the sinus rhythm capture threshold. For example, the energy of the pace pulses may be delivered at twice the sinus rhythm capture threshold, or a maximum pacing energy.

The pace pulses may be delivered at a pacing rate selected to produce capture of the atrium. In one example, the pace pulses are initially delivered at a predetermined percentage of the cardiac cycle length, such as 80-95% of the cardiac cycle length. The pacing rate may be adjusted to increase the cardiac cycle length prior to application of the cardioversion/defibrillation stimulation.

Following delivery of the pace pulses, capture of the arrythmic tissue is verified 320. The energy and frequency of the pace pulses are selected to capture all or a portion of the fibrillating tissue and thus "entrain" the cardiac activity. The evoked responses produced by the pace pulses represent more organized cardiac activity when compared to the chaotic activity of fibrillation. After entrainment, the pacing rate may be further adjusted to enhance organization while maintaining capture. If entrainment is not detected within a selected time interval, the pacing therapy may be terminated.

Capture verification may be implemented in the capture detector 224, shown in FIG. 2, using various techniques. The capture detector may detect various features of a cardiac waveform consistent with an evoked response morphology to determine if capture occurs at a pacing site. An exemplary set of features that may be used to determine capture include an amplitude of a cardiac signal, slope of the cardiac signal, timing of local maxima or minima of the cardiac signal, the rise time and/or fall times of the cardiac signal, or a curvature of the cardiac signal. Other features of the cardiac signal may also be used to determine capture.

In one embodiment, the capture detector determines capture has occurred by comparing an amplitude of a sensed cardiac signal within a specified time window following the stimulation pulse to an amplitude associated with an evoked response. If the sensed cardiac signal achieves the amplitude associated with the evoked response, indicating capture of the paced chamber or chambers, the capture detector determines that capture has occurred. In other embodiments, one or more time intervals between cardiac signal features may also be used to determine capture. Capture may also be determined by comparing a cardiac waveform produced by a stimulus pulse to an evoked response template waveform.

Following capture detection, a cardioversion/defibrillation stimulus is delivered 330 to the heart. In accordance with embodiments of the invention, detection of capture by one or more pace pulses triggers the delivery of the cardioversion/defibrillation stimulation. Entrainment may be verified if a series of pace pulses result in capture of the heart tissue. Triggering the cardioversion/defibrillation stimulation upon verification of successful entrainment may be used to ensure organization of cardiac activity prior to delivery of the cardioversion/defibrillation shock.

If the pace pulses applied capture a sufficient area of arrhythmic heart tissue, cardiac activity may be more organized, and a lower energy shock may be used to terminate the arrhythmia. Using lower energy stimulation to terminate the arrhythmia may be more comfortable for the patient and extend the battery life of the ICD.

The delivery of atrial therapy may be enhanced by synchronization of the cardioversion/defibrillation stimulation with a QRS complex. Synchronization of the cardioversion/defibrillation stimulation to a QRS complex decreases the likelihood of delivering the stimulation pulse during a period of ventricular vulnerability, a situation that may induce ventricular tachyarrhythmia.

As previously discussed, the pacing rate may be adjusted to increase the cardiac cycle length. According to this method, the pacing rate is established at a selected percentage of the cardiac cycle. Upon detection of capture, the pacing rate may be decreased, thus increasing the cardiac cycle length while capture is maintained.

Figure 4:
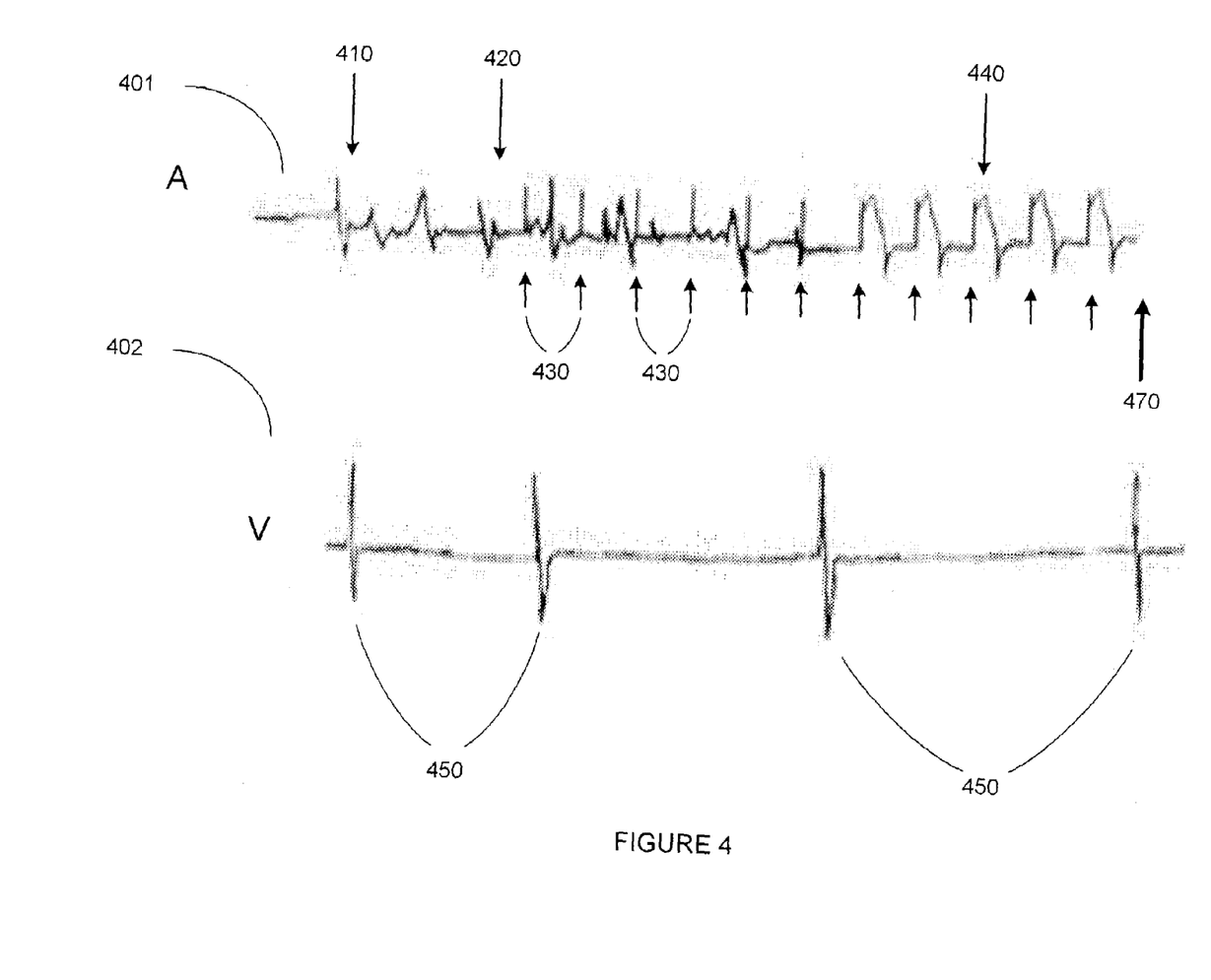
FIG. 4 is a graph illustrating the effect of pacing on cardiac activity during atrial fibrillation in accordance with embodiments of the invention.

FIG. 4 illustrates therapy delivery for atrial fibrillation in accordance with an embodiment of the invention. In this example, atrial 401 and ventricular 402 activity is illustrated in charts A and V, respectively. The ventricular activity includes a number of QRS complexes 450. Cardiac activity during atrial fibrillation 410 is characterized by rapid and disorganized depolarizations. Atrial fibrillation is detected 420 and pacing entrainment is attempted. A series of pacing pulses 430 are delivered to the atrium. In this example, the pacing activity in the atrium does not influence the innate ventricular activity.

After the pace pulses consistently capture the atrium 440, cardiac activity becomes more organized, but remains more rapid than a normal rate. The increased organization of the pace pulses decreases the energy required to terminate the atrial fibrillation. After entrainment is detected 440, delivery of the cardioversion/defibrillation stimulation 470 to the atrium is synchronized with a ventricular QRS complex 450.

Figure 5:
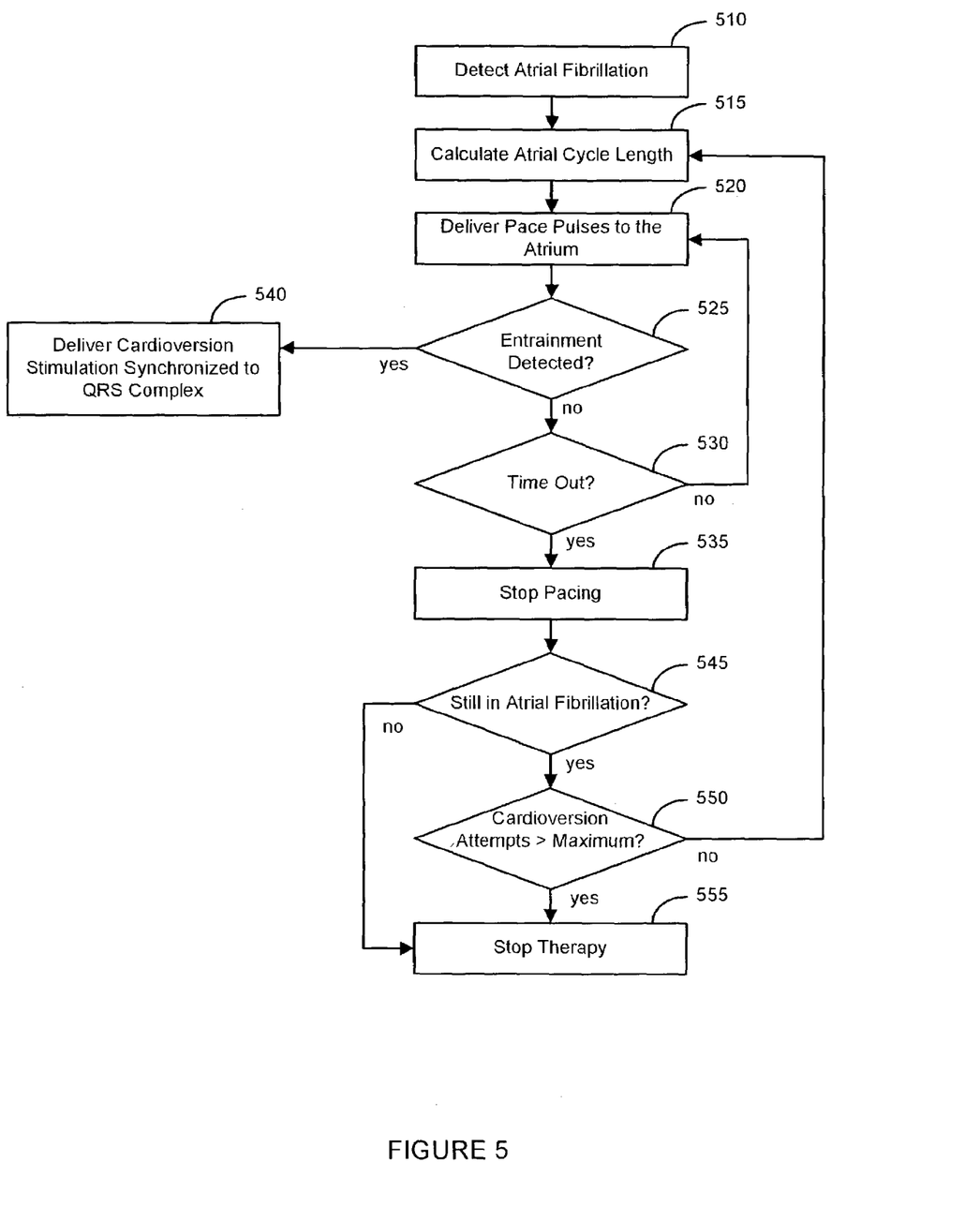
FIG. 5 is a flowchart of a method of providing atrial fibrillation therapy in accordance with embodiments of the present invention.

Cardioversion therapy to terminate atrial fibrillation in accordance with a embodiments of the invention is illustrated in FIG. 5. Although the example provided in FIG. 5 relates to atrial fibrillation therapy, the principles of the invention may be applied to alleviate tachyarrhythmia in any heart chamber or multiple heart chambers. Accordingly, following identification of a tachyarrhythmic episode occurring in one or more heart chambers, pace pulses are delivered to the arrhythmic chamber or chambers in an effort to organize the electrical activity of the heart. Cardioversion/defibrillation stimulation is delivered after verification that the cardiac activity of the chamber has become more organized, e.g., entrained by a series of pace pulses.

Turning now to FIG. 5, following detection of atrial fibrillation 510, the atrial cycle length is determined 515. One or more pace pulses are delivered 520 to the atrium during a predetermined time interval. The pace pulses may be delivered at a rate selected to produce and/or maintain capture of the atrium. The pacing interval may be adjusted to improve the organization and/or decrease the rate of atrial contractions before application of cardioversion therapy.

The system determines if the pace pulses consistently produce capture 525 in the atrium. When the pace pulses consistently produce capture, the atrium is considered to be entrained. In one example, if about three to five consecutive atrial pace pulses produce capture, the cardiac activity may be considered to be entrained by the pace pulses. Entrainment of the cardiac tissue by the pace pulses may increase the effectiveness of cardioversion therapy and/or lower the energy requirements of the therapy. If entrainment is detected, a cardioversion stimulation is delivered 540 to the heart synchronized to a QRS complex.

If entrainment does not occur 530 within the predetermined time period, pacing is terminated 535. The system determines if the heart remains in atrial fibrillation 545. If the heart remains in fibrillation, additional pacing followed by cardioversion stimulation may be delivered using the triggering method described at blocks 510-540. However, if the cardioversion attempts reach a maximum allowable number 550, for example, about five attempts, then the therapy is terminated 555.

Figure 6:
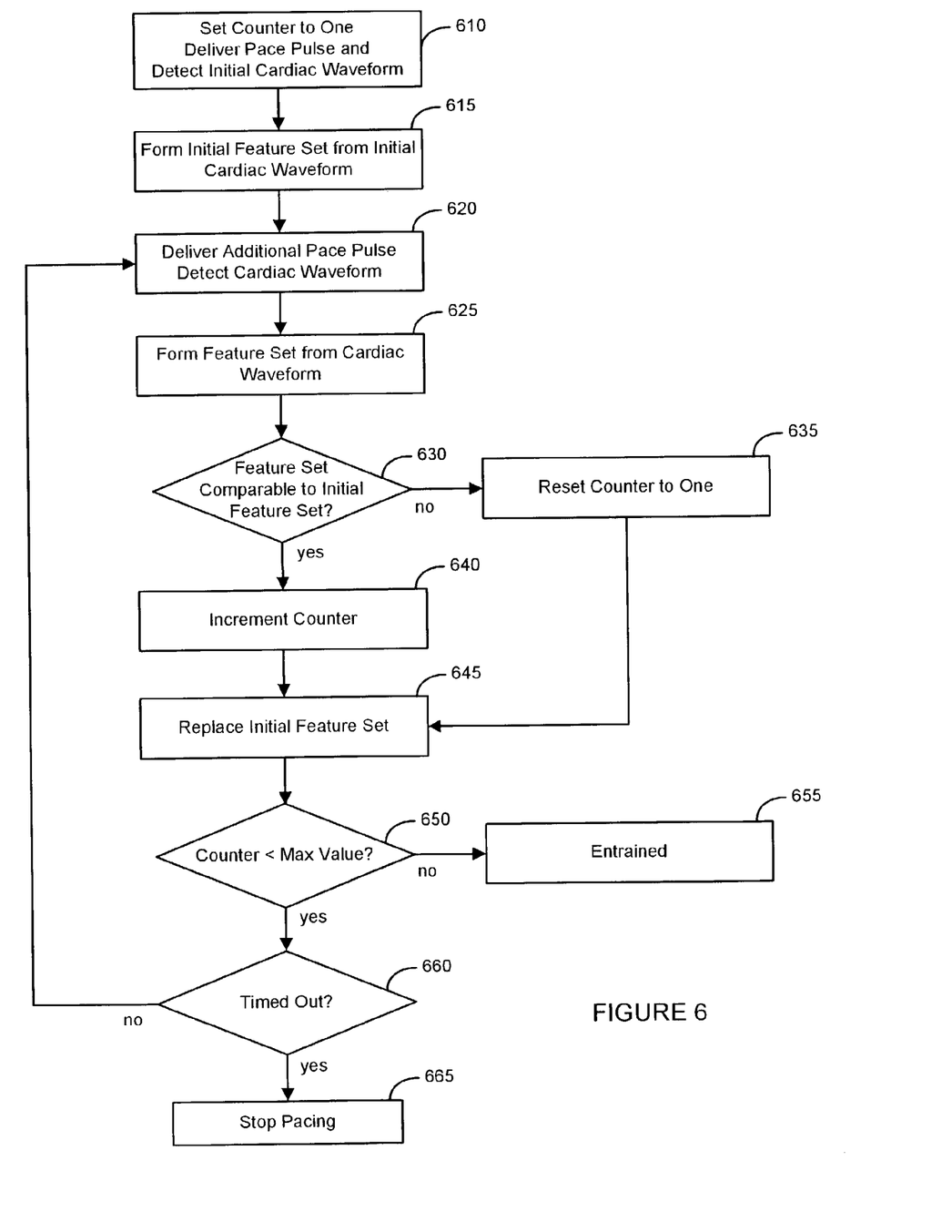
FIG. 6 is a flowchart of a method for determining entrainment by pace pulses delivered to the heart during an arrhythmic episode in accordance with embodiments of the invention.

A method for determining entrainment is illustrated in the flow chart of FIG. 6. Following the detection of a tachyarrhythmia, a counter is set to one and an initial pace pulse is delivered to the arrhythmic chamber. The cardiac waveform responsive to the initial pace pulse is detected 610 and an initial feature set is formed 615 from the detected cardiac waveform. The initial feature set may include such features as the amplitude, inflection points, slope, timing, and local extrema of the cardiac waveform.

An additional pace pulse is delivered and the cardiac waveform responsive to the additional pace pulse is detected 620. A feature set is extracted 625 from the cardiac waveform. If the feature set is of the cardiac waveform is consistent 630 with the initial feature set, then the counter is incremented 640 and the initial feature set is replaced 645 by the feature set acquired at block 625. If the feature set is not consistent with 630 the initial feature set, then the counter is reset to one 635 and the initial feature set is replaced 645 by the feature set acquired at block 625.

If the counter reaches 650 a maximum value during the predetermined therapy interval, then the cardiac activity is entrained 655 by the pace pulses. The maximum counter value may be in the range of about three to five, for example. If the counter has not reached the maximum value and the process has not timed out 660, then additional pace pulses are delivered and the responsive cardiac waveforms are detected and assessed according to the processes illustrated at blocks 620-655. However, if the process exceeds 660 the predetermined therapy interval, then pacing is discontinued 665.

The methods, devices, and systems of the invention described herein are particularly well-suited to therapies applied to terminate atrial arrhythmias, such as atrial fibrillation. However, the principles of the invention are also applicable to enhance anti-tachyarrhythmia therapy directed to any heart chamber. Further, the therapy is not limited to a single chamber, but may be applied to one or more chambers of the heart.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for providing cardiac therapy, comprising:
    detecting a tachyarrhythmic episode of an atrium of a heart;
    delivering pace pulses to the atrium during the tachyarrhythmia episode;
    after detecting the tachyarrhythmic episode, forming a morphological feature set from a subset of cardiac signals sensed following one or more of the pace pulses;
    evaluating capture of the atrium by each of the pace pulses based on whether features of a cardiac signal sensed following each of the pace pulses are consistent with the morphological feature set; and
    delivering cardioversion/defibrillation stimulation to the atrium responsive to the detection of capture.

2. The method of claim 1, wherein delivering the pace pulses comprises delivering the pace pulses in a timed relationship with tachyarrhythmic activity.

3. The method of claim 1, wherein delivering the pace pulses comprises delivering the pace pulses at an adaptable rate selected to organize electrical activation of the atrium.

4. The method of claim 3, wherein the adaptable rate is selected to produce capture.

5. The method of claim 3, wherein the adaptable rate is selected to increase an atrial cycle length.

6. The method of claim 1, wherein delivering the pace pulses to the atrium comprises:
    determining an atrial cycle length; and
    setting a pacing interval to a predetermined percentage of the atrial cycle length.

7. The method of claim 6, wherein the predetermined percentage is about 80-95%.

8. The method of claim 6, further comprising adapting the pacing interval based on current capture status.

9. The method of claim 1, wherein delivering the pace pulses to the atrium comprises delivering the pace pulses at an energy level about twice a sinus rhythm capture threshold energy level.

10. The method of claim 1, wherein delivering the pace pulses to the atrium comprises delivering the pace pulses at a maximum pacing level.

11. The method of claim 1, wherein delivering the cardioversion/defibrillation stimulation comprises delivering the cardioversion/defibrillation stimulation at a selectable energy level.

12. The method of claim 1, further comprising detecting that cardiac activity is entrained by the pace pulses.

13. The method of claim 12, wherein detecting that the cardiac activity is entrained comprises detecting capture of the atrium by a predetermined number of consecutive pace pulses.

14. The method of claim 13, wherein the predetermined number is about three to five.

15. The method of claim 13, wherein detecting that the cardiac activity is entrained comprises:
    forming feature sets characterizing the cardiac signals sensed following the pace pulses;
    comparing the feature sets; and detecting that the cardiac activity is entrained if a predetermined number of the feature sets associated with consecutive cardiac signals are consistent.

16. The method of claim 15, wherein the predetermined number is about three to five.

17. The method of claim 15, wherein the feature sets comprise one or more morphological features of the cardiac signals.

18. The method of claim 1, further comprising repeating the cardiac therapy a maximum number of times or until the tachyarrhythmia episode is terminated.

19. A method for providing tachyarrhythmia therapy to a heart, comprising:
   detecting a tachyarrhythmic episode of the heart;
   delivering pace pulses to the heart during the tachyarrhythmia episode;
   after detecting the tachyarrhythmic episode, forming a morphological feature set from a subset of cardiac signals sensed following one or more of the pace pulses;
   evaluating capture of the heart by each of the pace pulses based on whether features of a cardiac signal sensed following each of the pace pulses are consistent with the morphological feature set; and
   delivering cardioversion/defibrillation stimulation responsive to the detection of capture.

20. The method of claim 19, wherein:
   delivering the pace pulses to the heart comprises delivering the pace pulses to one or more heart chambers; and
   delivering the cardioversion/defibrillation stimulation comprises delivering the cardioversion/defibrillation stimulation to one or more heart chambers.

21. The method of claim 19, wherein:
   delivering the pace pulses to the heart comprises delivering the pace pulses to a ventricle; and
   delivering the cardioversion/defibrillation stimulation comprises delivering the cardioversion/defibrillation stimulation to the ventricle.

22. The method of claim 19, wherein delivering the pace pulses to the heart comprises delivering the pace pulses to one or more tachyarrhythmic chambers of the heart.

23. The method of claim 19, wherein delivering the cardioversion/defibrillation stimulation comprises delivering the cardioversion/defibrillation stimulation to one or more tachyarrhythmic chambers of the heart.

24. The method of claim 19, wherein delivering the pace pulses to the heart comprises delivering the pace pulses in a timed relationship with tachyarrhythmic activity.

25. The method of claim 19, wherein delivering the pace pulses to the heart comprises delivering the pace pulses at an adaptable rate selected to organize electrical activation of the heart.

26. The method of claim 19, wherein delivering the pace pulses to the heart comprises delivering the pace pulses at a rate selected to produce capture.

27. The method of claim 19, wherein the delivering the pace pulses to the heart comprises delivering the pace pulses at a rate selected to increase a cardiac cycle length.

28. The method of claim 19, wherein delivering the pace pulses to the heart comprises:
   determining a cardiac cycle length; and
   setting a pacing interval to a predetermined percentage of the cardiac cycle length.

29. The method of claim 28, wherein the predetermined percentage is about 80-95%.

30. The method of claim 28, wherein setting the pacing interval comprises adapting the pacing interval to produce capture based on current capture status.

31. The method of claim 19, wherein delivering the pace pulses to the heart comprises delivering the pace pulses at a selectable energy level.

32. The method of claim 31, wherein the selectable energy level is about twice a sinus rhythm capture threshold.

33. The method of claim 31, wherein the selectable energy level is a maximum pacing level.

34. The method of claim 19, wherein delivering the cardioversion/defibrillation shock comprises delivering the cardioversion/defibrillation shock at a selectable energy level.

35. The method of claim 19, further comprising detecting that cardiac activity is entrained by the pace pulses.

36. The method of claim 35, wherein detecting that the cardiac activity is entrained comprises detecting capture of the heart by a predetermined number of consecutive pace pulses.

37. The method of claim 36, wherein the predetermined number is in the range of about three to five.

38. The method of claim 35, wherein detecting that the cardiac activity is entrained comprises:
   forming feature sets characterizing the cardiac signals sensed following the pace pulses;
   comparing the feature sets; and
   detecting that the cardiac activity is entrained if a predetermined number of the feature sets characterizing consecutive cardiac signals are consistent.

39. The method of claim 38, wherein the predetermined number is about three to five.

40. The method of claim 38, wherein the feature sets comprise one or more morphological features of the cardiac signals.

41. The method of claim 19, further comprising repeating the tachyarrhythmia therapy a maximum number of times or until the tachyarrhythmia episode is terminated.

42. A therapy system, comprising:
   means for detecting a tachyarrhythmic episode of an atrium of a heart; means for delivering pace pulses to the atrium during the tachyarrhythmia episode;
   means for forming, after detecting the tachyarrhythmic episode, a morphological feature set from a subset of cardiac signals sensed following one or more of the pace pulses;
   means for evaluating capture of the atrium by each of the pace pulses based on whether features of a cardiac signal sensed following each of the pace pulses are consistent with the morphological feature set; and
   means for delivering cardioversion/defibrillation stimulation to the atrium responsive to the detection of capture.

43. An system for providing therapy to a heart, comprising:
   means for detecting a tachyarrhythmic episode of the heart;
   means for delivering pace pulses to the heart during the tachyarrhythmia episode;
   means for forming, after detecting the tachyarrhythmic episode, a morphological feature set from a subset of cardiac signals sensed following one or more of the pace pulses;
   means for evaluating capture of the heart by each of the pace pulses based on whether features of a cardiac signal sensed following each of the pace pulses are consistent with the morphological feature set; and
   means for delivering cardioversion/defibrillation stimulation responsive to the detection of capture.

* * * * *